United States Patent
Smith et al.

(10) Patent No.: US 8,460,702 B2
(45) Date of Patent: Jun. 11, 2013

(54) PHARMACEUTICAL COMPOSITIONS

(75) Inventors: Alan Smith, Nottingham (GB); Ann Margaret Dyer, Nottingham (GB)

(73) Assignee: Archimedes Development Limited, Nottingham (GB)

(*) Notice: Subject to any disclaimer, the term of this patent is extended or adjusted under 35 U.S.C. 154(b) by 273 days.

(21) Appl. No.: 12/097,163

(22) PCT Filed: Dec. 15, 2006

(86) PCT No.: PCT/GB2006/004710
§ 371 (c)(1),
(2), (4) Date: Oct. 30, 2008

(87) PCT Pub. No.: WO2007/068948
PCT Pub. Date: Jun. 21, 2007

(65) Prior Publication Data
US 2009/0130202 A1  May 21, 2009

(30) Foreign Application Priority Data
Dec. 15, 2005  (GB) .................................. 0525461.0

(51) Int. Cl.
*A61K 9/64* (2006.01)
*A61K 9/14* (2006.01)

(52) U.S. Cl.
USPC .......................................... 424/456; 424/489

(58) Field of Classification Search
None
See application file for complete search history.

(56) References Cited

U.S. PATENT DOCUMENTS

| | | | |
|---|---|---|---|
| 5,324,522 A | 6/1994 | Krenning et al. | |
| 5,753,254 A * | 5/1998 | Khan et al. | 424/439 |
| 6,190,696 B1 * | 2/2001 | Groenewoud | 424/464 |
| 6,288,117 B1 | 9/2001 | Klein et al. | |
| 6,469,035 B1 * | 10/2002 | Cefali | 514/356 |
| 6,500,459 B1 * | 12/2002 | Chhabra et al. | 424/474 |
| 6,558,659 B2 * | 5/2003 | Fox et al. | 424/78.31 |
| 6,646,007 B1 * | 11/2003 | Schreder et al. | 514/567 |
| 2006/0246133 A1 * | 11/2006 | Beasley et al. | 424/468 |

FOREIGN PATENT DOCUMENTS

| | | |
|---|---|---|
| EP | 0305051 A1 | 3/1989 |
| EP | 0 550 108 A1 | 7/1993 |
| JP | 05-255081 A | 10/1993 |
| JP | 2002-526402 A | 8/2002 |
| WO | 8808299 A1 | 11/1988 |
| WO | 99/36060 A1 | 7/1999 |
| WO | 0019985 A2 | 4/2000 |
| WO | 01/13897 A1 | 1/2001 |
| WO | 0174329 A2 | 10/2001 |
| WO | WO 01/74329 * | 10/2001 |

(Continued)

OTHER PUBLICATIONS

Hercules, "Aqualon Ethylcellulose (EC) Physical and Chemical Properties," 2002, pp. 1-35.*

(Continued)

*Primary Examiner* — Brian Gulledge
(74) *Attorney, Agent, or Firm* — Panitch Schwarze Belisario & Nadel LLP

(57) ABSTRACT

Sustained release pharmaceutical compositions contain a drug; microcrystalline cellulose; a diluent (such as starch); a glidant (such as talc); and one or more of ethylcellulose, stearic acid and a salt of stearic acid. Preferred drugs include those that exhibit a low degree of solubility combined with a high potency, particularly thyroid hormones, such as liothyronine.

27 Claims, 9 Drawing Sheets

FOREIGN PATENT DOCUMENTS

| WO | 03/075830 | A2 |   | 9/2003 |
|----|-----------|----|---|--------|
| WO | WO 03/075830 |  | * | 9/2003 |
| WO | 2004/043452 | A1 |   | 5/2004 |
| WO | 2006/105482 | A2 |   | 5/2006 |

OTHER PUBLICATIONS

Office Action issued Aug. 19, 2010 in IL Application No. 192091, 2 pages.

Venkatraman et al., "An Overview of Controlled Release Systems" in WISE, Ed., Handbook of Pharmaceutical Controlled Release Technology, (2000), pp. 435-445, Marcel Dekker, Inc., N.Y., New York.

Qiu et al., "Research and Development Aspects of Oral Controlled-Release Dosage Forms" in WISE, Ed., Handbook of Pharmaceutical Controlled Release Technology, (2000), pp. 466-503, Marcel Dekker, Inc., N.Y., New York.

Charman et al., "Oral Modified-Release Delivery Systems" in Rathbone et al., Modified-Release Drug Delivery Technology, (2003), pp. 1-10, Marcel Dekker, Inc., N.Y., New York.

Duane D. Miller, PhD., "Structure-Activity Relationship and Drug Design," (2000) Chapter 28, pp. 458-468, in Gennaro, Ed., 20th Edition, Remington: The Science and Practice of Pharmacy, Lippincott Williams & Wilkins, Philadelphia.

Rudnic, et al. "Oral Solid Dosage Forms," (2000) Chapter 45, pp. 858-2712, in Gennaro, Ed., 20th Edition, Remington: The Science and Practice of Pharmacy, Lippincott Williams & Wilkins, Philadelphia.

Zhang et al., "Studies on the cyclosporin A loaded stearic acid nanoparticles," International Journal of Pharmaceutics 200 (2000) pp. 153-159, Elsevier Science B.V.

Bargoni et al., "Solid Lipid Nanoparticles in Lymph and Plasma After Duodenal Administration to Rats," Pharmaceutical Research, vol. 15, No. 5 (1998) pp. 745-750, Plenum Publishing Company.

Schwarz et al., "Freeze-drying of drug-free and drug-loaded solid lipid nanoparticles (SLN)," International Journal of Pharmaceutics 157, (1997), pp. 171-179, Elsevier Science B.V.

United States Pharmacopeia, USP28 (2005), pp. 2412-2414.

United States Pharmacopeia, USP28 (2005), p. 2712.

Office Action issued May 31, 2011 in IL Application No. 192091.

Office Action issued Nov. 17, 2011 in EP Application No. 06820546.7.

Notice of Allowance issued Jan. 4, 2012 in IL Application No. 192091.

Office Action issued Nov. 17, 2011 in EP Application No. 06 820 546.7.

Office Action issued Jun. 19, 2012 in JP Application No. 2008-545097.

Nankado Inc., Shin Yakuzaigaku Saiton, pp. 262-266 (Apr. 10, 1987).

Yang et al, Zhongguo Yiyuan Yaoxue Zazhi, vol. 18, No. 7, pp. 343-314 (1998).

Starha et al, Csesko-Slovenska Farmacie, vol. 20, No. 2, pp. 60-62 (1971).

Office Action issued Oct. 18, 2012 in CA Application No. 2,634,006.

English translation of an Office Action issued Dec. 25, 2012 in JP Application No. 2008-545097.

Zhang et al, "Studies on the cyclosporin A loaded stearic acid nanoparticles", International Journal of Pharmaceutica, vol. 200, pp. 153-159 (2000).

Office Action issued Jan. 10, 2013 in IN Application No. 5139/DELNP/2008.

* cited by examiner

US 8,460,702 B2

PHARMACEUTICAL COMPOSITIONS

CROSS-REFERENCE TO RELATED APPLICATIONS

This application is a Section 371 of International Application No. PCT/GB2006/004710, filed Dec. 15, 2006, which was published in the English language on Jun. 21, 2007, under International Publication No. WO 2007/068948 A2 and the disclosure of which is incorporated herein by reference.

BACKGROUND OF THE INVENTION

This invention relates to novel pharmaceutical formulations that are useful in particular in the oral administration of thyroid hormones.

The principal role of the thyroid gland is to regulate tissue metabolism through production of thyroid hormones. The main hormone produced is 3,5,3',5'-tetraiodo-L-thyronine (L-thyroxine; T4) with smaller amounts of 3,5,3'-triiodo-L-thyronine (liothyronine; T3) also being produced. The hormones are produced utilising dietary iodine, which is absorbed from the gastrointestinal tract as iodide and transported into the thyroid gland.

Whilst T4 enters the circulation only by way of direct glandular secretion, very little T3 is secreted by the thyroid gland, with most extra-glandular T3 being produced by deiodination of circulating T4. The metabolic activity of T3 is about 3 to 5 times higher than T4 and it has been postulated that T3 is the active hormone, with T4 acting largely as a pro-drug.

Synthetically-produced T3 and T4 are employed in the treatment of hypothyroidism. The low endogenous production of thyroid hormone gives rise to symptoms associated with a slow metabolism, such as fatigue (including muscle fatigue), weight gain and/or increased difficulty losing weight, coarse/dry hair and/or hair loss, dry/rough/pale skin, cold temperature intolerance, muscle cramps and/or frequent muscle aches, constipation, depression, irritability, memory loss, abnormal menstrual cycles and decreased libido.

This extremely common condition may result from inflammatory diseases of the thyroid, such as autoimmune thyroiditis, or as a side effect following certain medical treatments.

When given as a replacement therapy in the treatment of hypothyroidism, the optimum effects of T4 may not be achieved for several weeks and there is a slow response to changing dosage.

T3, on the other hand, is administered to achieve a more rapid effect and/or a shorter duration of action. It is typically administered in the form of the sodium salt at an initial adult dose of 5 to 25 µg daily, increased gradually to a maintenance dose of 60 to 75 µg (although up to 100 µg may be required in some patients).

High concentrations of circulating T3 resulting from oral administration of conventional T3-containing immediate release tablet formulations (which provide for the equivalent of between 5 and 50 µg of T3) are associated with side effects, particularly in patients with angina or ischemic heart disease, or where infarction or dysrhythmia may prove fatal.

Congestive heart failure exhibits high mortality and increasing prevalence. The use of T3 in the treatment of this condition has been described. However, in order to be safe and effective in such treatment, the circulating concentration of T3 must remain within a narrow and specific therapeutic window. A sustained release oral dosage form is required to facilitate this.

Sustained release or extended release oral dosage forms, which are used to control (i.e. slow) the rate at which an orally administered drug compound is absorbed into the systemic circulation, are widely described in the scientific and patent literature (see, for example, Venkatraman et al, *Handbook of Pharmaceutical Controlled Release Technology*, Wise (Ed.), Marcel Dekker, New York, 2000, pp. 435-445; Qiu and Zhang, ibid., pp. 465-503; Charman and Charman, *Modified-Release Drug Delivery Technology*, Rathbone et al (Eds.), Marcel Dekker, New York, 2003, pp. 1-10).

Two consequences of slowing the rate of absorption are: (a) a reduction in the peak blood level of drug ($C_{max}$) relative to the same dose of drug administered by way of an immediate release dosage form; and (b) an extended duration of circulation of drug in the systemic circulation. The latter may result in a potential reduction in dosing frequency.

Basic approaches for producing sustained release dosage forms include matrix systems, which typically comprise drug encapsulated in insoluble, slowly eroding and/or swelling materials (often polymers); reservoir systems, including polymer coated tablets, pellets or granules; ion-exchange systems; and osmotic systems.

In order to function optimally, many of these approaches rely on the drug that is employed having a reasonable solubility in aqueous media. Providing a sustained release dosage form for use with poorly-soluble drug compounds presents more of a challenge and, accordingly, formulation options for use with such drugs are more limited (see Qiu and Zhang above).

Recent innovations in drug discovery, such as combinatorial chemistry and high-throughput screening, have resulted in more efficient and effective means of drug-lead generation and the optimisation of new drug-lead molecules (see, for example, Remington, *The Science and Practice of Pharmacy*, $20^{th}$ Edition, Chapter 28, Lippincott Williams & Wilkins (Ed.), Philadelphia, 2000). However, although highly potent compounds have frequently been identified using these technologies, such compounds have often been found to exhibit extremely low aqueous solubility.

BRIEF SUMMARY OF THE INVENTION

Thus, there is a need generally for improved sustained release dosage forms for poorly-soluble drug compounds, in particular for administration via the oral route.

Ethylcellulose (EC) is a non-ionic ethyl ether of cellulose. It is a water insoluble polymer and is pH insensitive. Common applications of ethylcellulose include microencapsulation, taste masking, compression coating, sustained release direct compression tablets and film coatings. Its use in sustained-release bead matrices prepared by extrusion-spheronization in combination with microcrystalline cellulose, a diluent and high concentrations of a glidant has not, to the applicant's knowledge, been disclosed or suggested previously.

Stearic acid and its salts, such as magnesium, calcium and zinc stearates, are hydrophobic materials that are typically used in orally administered pharmaceutical dosage forms as lubricants. They are used in such applications in only small amounts, typically at up to 5% by weight. The use of stearic acid for making drug-containing nanoparticles has been described (see e.g. Zhang et al, *Int. J. Pharm.*, 200, 153-159, 2000; Bargoni et al, Pharm. Res., 15, 745-750, 1998; and Schwarz and Wehnert, *Int. J. Pharm.*, 157, 171-179, 1997).

We have found, surprisingly, that when used in combination with appropriate additional excipients, stearic acid and its salts may impart sustained release characteristics in oral dosage forms, such as pellets, granules and tablets.

The use of sustained release dosage forms to deliver T3 is described in U.S. Pat. Nos. 6,288,117 and 5,324,522. However, compositions comprising one or more of ethylcellulose, stearic acid and a salt of stearic acid, in combination with microcrystalline cellulose, a diluent such as starch and a glidant such as talc, are not disclosed in either of these documents.

According to a first aspect of the invention, there is provided a sustained release pharmaceutical composition suitable for use with poorly soluble and/or highly potent drugs, which composition comprises a drug; microcrystalline cellulose; a diluent; a glidant; and a matrix-forming material selected from one or more of ethylcellulose, stearic acid and a salt of stearic acid, which compositions are referred to hereinafter as "the compositions of the invention".

The term "sustained release" will be well understood by the skilled person to include any composition/formulation in which the onset and/or rate of release of drug is altered by galenic manipulations, and thus includes the definition of "extended-release tablets" provided at page 2712 of the *United States Pharmacopoeia* (USP 28, 2005): "Extended-release tablets are formulated in such a manner as to make the contained medicament available over an extended period of time following ingestion. Expressions such as "prolonged-action", "repeat-action" and "sustained-released" have also been used to described such dosage forms." The term "sustained release" thus applies to dosage forms in which drug is released at a sufficiently retarded rate to produce a therapeutic response over a required period of time.

Drug compounds that may be delivered by way of the compositions of the invention include those that are poorly soluble in aqueous media. The term "poorly soluble" as employed in the present context indicates that the drug compound exhibits a solubility in water and/or a simulated gastrointestinal medium (for example as described below) of less than 1 mg/ml at a temperature of 37° C. and at atmospheric pressure. Simulated gastrointestinal media include 0.1 molar hydrochloric acid and buffer solutions in the pH range of 2 to 8. Such media may also contain enzymes and are described in the *United States Pharmacopoeia* (USP 28, 2005).

The compositions of the invention are preferably adapted for oral delivery in the form of granules, tablets or, most preferably, pellets.

The term "pellets" includes more than one spherical or substantially spherical particulate composition comprising drug and other ingredients mentioned hereinbefore. Techniques for producing pellets include spray drying, spray congealing, melt-cooling and extrusion-spheronization.

The preferred process for making compositions of the invention in the form of pellets is extrusion-spheronization. This technique enables the formation of uncoated spherical particles with regularity of shape, uniformity of size and smooth surface characteristics. These particles have low friability and are associated with few fines. These characteristics mean that the pellets are also an excellent substrate for the application of film coatings to provide modified release properties. Pellets have an additional advantage of less variable transit through the gastrointestinal tract than large single-unit dosage forms such as non-disintegrating tablets and capsules and hence provide the potential for more uniform drug absorption.

Thus, the present invention provides a sustained release pharmaceutical composition comprising a drug, a microcrystalline cellulose, a diluent, a glidant; and one or more ethylcellulose, stearic acid and a salt of stearic acid obtainable by a process comprising extrusion-spheronization. The extrusion-spheronization process typically produces the compositions of the invention in the form of pellets.

We have found that the use of extrusion-spheronization facilitates the formation of pellets exhibiting reproducible homogeneity for high potency (i.e. low dose) drugs, and which contain high amounts of the sustained release material(s) mentioned hereinbefore.

In this process, a heavy granule or wet mass is made by mixing drug and the relevant excipients with sufficient water to form a paste. This is then passed through an extruder. The extrudate is transferred to a spheronizer. This equipment comprises a horizontally spinning metal disc having a scored surface, which is typically cross-hatched. When applied to this spinning surface, the extrudate is broken up and transformed into essentially spherical particles, which are then dried to remove water. The pellet diameter produced by way of this process is preferably in the range 0.05 to 3 mm, more preferably 0.075 to 2.5 mm, and most preferably 0.1 to 2 mm.

Compositions of the invention in the form of pellets are preferably administered in hard capsules made, for example, of gelatin, hydroxypropylmethylcellulose, pullulan or starch. Thus, the present invention provides hard capsules made, for example, of gelatin, hydroxypropylmethylcellulose, pullulan or starch which comprise a composition of the invention obtainable by a process comprising extrusion-spheronization.

The preparation of tablet and granule formulations is well known to those skilled in the art. Further details can be found in standard texts, such as Remington, *The Science and Practice of Pharmacy* (Chapter 45, Lippincott Williams & Wilkins (Ed.), Philadelphia, 2000).

For example, compositions of the invention in the form of tablets may be prepared by compressing a blend of the individual ingredients or by compressing granules or a blend of granules comprising some of the ingredients i.e. some of the ingredients are "intra-granular" and others are "extra-granular". Alternatively, compositions of the invention in the form of pellets may be blended with appropriate ingredients and compressed into a tablet.

The compositions of the invention may comprise ethylcellulose as the only matrix-forming material. Alternatively, ethylcellulose can be used in combination with stearic acid and/or a salt of stearic acid. In another alternative, stearic acid may be used as the only matrix-forming material. Stearic acid may also be used in combination with a salt of stearic acid and/or ethylcellulose. In yet another alternative, a salt of stearic acid may be used as the only matrix-forming material. A salt of stearic acid may be used in combination with stearic acid and/or ethylcellulose.

Compositions of the invention typically comprise one or more of ethylcellulose, stearic acid and a salt of stearic acid in an amount such that the total weight of these components in the composition is greater than 5 up to about 70% w/w, preferably from about 10 to about 60% w/w, and more preferably from about 20 to about 50% w/w, based on the total weight of the composition.

In a particular aspect of the present invention there is provided a sustained release pharmaceutical composition comprising a drug, microcrystalline cellulose, a diluent, a glidant and one more of ethylcellulose, stearic acid and a salt of stearic acid obtainable by a process comprising extrusion-spheronization wherein one or more of ethylcellulose, stearic acid and a salt of stearic acid is present in an amount such that the total weight of these components in the composition is greater than 5 up to about 70% w/w, preferably from about 10 to about 60% w/w, and more preferably from about 20 to about 50% w/w, based on the total weight of the composition.

In a specific aspect of the invention, the compositions comprise ethylcellulose in the absence of stearic acid and in the absence of a salt of stearic acid. Such compositions are preferably in the form of pellets. These pellets are, for example, obtainable by a process comprising extrusion-spheronization.

Particularly preferred pellets of the invention consist essentially of a drug, microcrystalline cellulose, a diluent, a glidant, and ethylcellulose.

Preferred types of ethylcellulose that may be used have a low viscosity in organic solvent (which is a measure of molecular weight), as well as a high ethoxyl content. These features provide the ethylcellulose with improved compactability and powder flow. The ethoxyl content (ethoxyl substitution) of the ethylcellulose is preferably in the range of from 44 to 51%, more preferably in the range of from 47 to 51% and most preferably in the range of from 49 to 51%, for example from 49.6 to 51.0%. The viscosity of the ethylcellulose (5% solution in 80/20 toluene/ethanol) is preferably in the range of from 2 to 40 cps, more preferably in the range of from 5 to 20 cps and most preferably in the range of from 7 to 14 cps, for example from 8 to 11 cps. An example of such an ethylcellulose is Aqualon® T10 EC, produced by Hercules, Inc (Wilmington, Del., USA). This has an ethoxyl substitution in the range 49.6 to 51.0% and a viscosity (5% solution in 80/20 toluene/ethanol) of 8-11 cps.

We have found that progressive slowing of drug release is observed in compositions of the invention with increasing levels of stearic acid up to about 30% w/w. Surprisingly, concentrations of stearic acid in excess of about 30% w/w may result in a progressive increase in the rate of drug release, which may be due to an increasing tendency for the dosage form to partially disintegrate. Preferably, the compositions of the invention that comprise stearic acid comprise from about 5 to about 25% w/w stearic acid, for example from about 5 to about 15 w/w or from about 10 to about 20% w/w, 25% w/w or 30% w/w, or from about 10 to about 15% w/w.

Progressive slowing of drug release is also observed from compositions with increasing levels of stearic acid salts. The maximum amount of stearic acid salts that may be included in a composition of the invention is in the region of about 50% w/w, based on the total weight of the composition. Levels in excess of this can render processing difficult. Compositions containing greater than about 50% w/w of stearic acid salts, based on the total weight of the composition, are typically non-disintegrating. However, compositions containing a mixture of calcium stearate and stearic acid do partially disintegrate during in vitro dissolution testing. The compositions of the invention that comprise stearic acid salts preferably comprise from about 5 to about 45% w/w stearic acid salts, for example from about 10 to about 35% w/w or from about 15 to about 30% w/w.

When stearic acid and stearic acid salts are both present in the compositions of the invention, there is typically more stearic acid salts than stearic acid. The amount of stearic acid and stearic acid salts is as described above and additionally, the ratio of stearic acid salts to stearic acid is preferably in the range of from about 1:1 to about 5:1 by weight, for example from about 1.5:1 to about 4:1 or from about 2:1 to about 3:1.

The compositions of the invention contain microcrystalline cellulose. We have found that microcrystalline cellulose, when employed in compositions of the invention in the form of pellets, acts as a spheronization enhancer, imparts binding properties necessary for pellet strength and integrity, and confers the plasticity necessary for extrudate and sphere formation. Preferably, the compositions of the invention comprise from 5 to 70% w/w of microcrystalline cellulose, more preferably from 10 to 60% and most preferably from 20 to 50% w/w, based on the total weight of the composition.

The incorporation of the inert glidant of the compositions of the invention ensures satisfactory and reproducible content uniformity by ensuring acceptable blend homogeneity during processing. The term "glidant" will be understood by those skilled in the art to include a material that is primarily employed in oral solid dosage forms to improve the flow properties of a powder blend, particularly in the presence of high concentrations of hydrophobic excipients, and therefore aids trituration and blending prior to, e.g., pelletization. Preferably, the glidant is able to facilitate mixing or blending processes in manufacturing operations for potent drugs.

Glidants that may be employed in the present invention include but are not limited to, colloidal silicon dioxide, magnesium stearate and, particularly, talc.

Preferably, the compositions of the invention comprise from 2 to 30% w/w of glidant, such as talc, more preferably from 5 to 25%, and particularly from 10 to 20% w/w, based on the total weight of the composition.

The compositions of the invention also comprise inert diluents. The term "diluent" will be understood by the skilled person to include a material that is primarily used in oral solid dosage forms as an inert filler. Preferably, the diluent should be able to facilitate mixing or blending processes in manufacturing compositions of the invention comprising potent drugs.

Diluents that may be employed in the present invention include, but are not limited to, starch, such as maize or corn starch, potato starch, rice starch, tapioca starch and wheat starch; lactose and other sugars, such as compressible sugar and dextrates; inorganic salts, such as dibasic calcium phosphate and tribasic calcium phosphate; cellulose; and polyols, such as mannitol, sorbitol and xylitol.

Preferably, the compositions of the present invention comprise from 5 to 60% w/w of diluent, such as starch, more preferably from 10 to 50% and most preferably from 15 to 35%, based on the total weight of the composition. The use of starch, and especially maize starch is preferred.

The choice and amount of individual ingredients that may be used in compositions of the invention will depend largely upon the physicochemical properties of the drug, specifically the solubility and dose of the drug, and the desired in vitro and in vivo release profiles. However, these can be determined routinely by the skilled person from within the ranges mentioned hereinbefore without recourse to inventive input.

Other considerations may include the physical and chemical compatibility of the relevant excipients with the drug and, if relevant, the suitability of the relevant material for processing by extrusion-spheronization. For example, it will be well known to the skilled person that excipients may exert an influence on the stability of the finished product, its bioavailability profile, and the ease with which it can be manufactured. For compositions of the invention in the form of pellets or beads, excipients of the pellet or bead core formulation should be capable of imparting the binding properties necessary for pellet or bead strength and integrity, as well as conferring the plasticity necessary for extrudate and sphere formation.

Other pharmaceutical excipients may be also be employed, including polysaccharides such as chitosan and chitin derivatives and pectin; xanthan, acacia, tragacanth, locust bean and guar gums; stearates such as, calcium and zinc stearates, and sodium stearyl fumarate; and hydrogenated vegetable oil.

Typical daily doses of drugs that may be employed in the compositions of the invention are preferably in the range 0.001 mg to 5000 mg, more preferably in the range 0.002 mg to 3000 mg, and most preferably in the range 0.003-2000 mg. The drug content of compositions of the invention is preferably in the range 0.0005-90% w/w, more preferably in the range 0.001-60% w/w and most preferably in the range 0.002-50% w/w, based on the total weight of the composition.

A non-exhaustive list of drugs that may be employed, as well as their doses may found in general texts, such as Martindale, *The Complete Drug Reference*, 34$^{th}$ Edition, Pharmaceutical Press (2005). Information on the solubility of drug compounds may be found in a publication such as *The Merck Index*, 12th Edition, Merck & Co., NJ, USA, 1996.

Compositions of the invention may provide for a "medium" sustained release or a "slow" sustained release of drug. By "medium sustained release" or "MSR", we mean that the composition exhibits a release in an in vitro dissolution test of at least 50% of drug within a period of around 4 hours, and at least 70% within a period of around 6 hours. By "slow sustained release" or "SSR", we mean that the composition exhibits corresponding release of at least 50% of drug within a period of around 8 hours and at least 70% within a period of around 12 hours.

It will be appreciated that all of the above-mentioned times are approximate, and that compositions may release the specified minimum amounts of drug within times which vary from the numbers specified above by ±20%, such as ±10%, e.g. ±5%. All such variations are intended to be encompassed by the use of the term "around".

An appropriate in vitro dissolution test is the Type I/II apparatus, as described in the *United States Pharmacopoeia* 28 (<711> pp. 2412-2414), using pH 7.4 phosphate buffer at 37° C. as the release medium.

Preferred drugs include thyroid hormones, and in particular T3. Unless otherwise indicated herein, the term "T3" refers to liothyronine or salts thereof. Unless otherwise indicated herein, amounts of T3 are expressed as free liothyronine. The sodium salt of liothyronine is the preferred form of T3.

MSR compositions of T3 preferably comprise ethylcellulose as the rate-controlling ingredient in combination with microcrystalline cellulose, starch and talc. A preferred MSR composition comprises 0.001 to 1% w/w of T3; 20 to 40% w/w of microcrystalline cellulose; 15 to 55% w/w of (e.g. maize) starch, 10-20% w/w of talc; and 15 to 25% w/w of ethylcellulose.

SSR compositions of T3 preferably comprise stearic acid and/or a salt thereof as the rate-controlling ingredient in combination with microcrystalline cellulose, starch and talc. A preferred SSR composition comprises 0.001 to 1% w/w of T3; 20 to 40% w/w of microcrystalline cellulose; 15 to 35% w/w of (e.g. maize) starch, 5 to 20% w/w of talc; 10 to 30% w/w of calcium stearate; and 5 to 15% w/w of stearic acid.

As a sustained release dosage form moves through the gastrointestinal tract it will be exposed to different pH values i.e. the gastric environment is acidic whereas the pH in the intestines is generally in the range 5-8. It is therefore highly desirable that a sustained release dosage form exhibits drug release properties that are independent of pH. It has been found that certain sustained release T3 compositions described earlier in this application may have drug release characteristics that are pH-dependent such that the rate of release is faster in acidic conditions that represent the stomach. To eliminate this effect, such T3 compositions, for example pellets, may optionally have an outer coating of gastro-resistant ("enteric") polymer applied. The application of such a polymer layer will prevent release of drug in the acidic stomach environment. However, the composition of the polymer layer is chosen such that it will rapidly dissolve in the small intestine allowing release of T3 to commence with minimal delay.

Suitable gastro-resistant polymers include methacrylic acid copolymers, cellulose acetate phthalate, cellulose acetate butyrate, hydroxypropylmethylcellulose phthalate and shellac. Especially preferred coating materials for use with T3 compositions are hydroxypropyl methylcellulose phthalate (HPMCP) 50, HPMCP 55 and methacrylic acid copolymer type C, USP e.g. Eudragit® L100-55 (registered trade mark of Degussa, Darmstadt, Germany). These polymers begin dissolving at around pH 5, pH 5.5 and pH 5.5 respectively and so their use should ensure rapid commencement of T3 release when the coated composition enters the small intestine from the stomach. The layer of coating polymer will typically also contain one or more of a plasticiser such as triacetin or a phthalate ester or polyethylene glycol, an anti-tack agent such as talc or magnesium stearate or colloidal silica, an anti-foaming agent and a colorant.

The amount of gastro-resistant polymer layer applied to the T3 compositions is preferably in the range 1-20%, more preferably in the range 1.5-15% and most preferably in the range 2-10%. These quantities relate to polymer alone and exclude added materials such as plasticiser and anti-tack agent. For example, a HPMCP coating may comprise approximately 50% w/w of polymer and 50% w/w of other additives.

Specifically, the compositions of the invention provide for commercially viable, once daily oral multiparticulate sustained release compositions containing 5 mcg of T3 per 50 mg unit dose, and exhibiting in vitro drug release over 6 to 8 hours (MSR compositions) and 12 to 18 hours (SSR compositions).

Thus, compositions of the invention comprising T3 are preferably in the form of pellets produced by extrusion-spheronization. The preferred process for making the pellets comprises in the first instance making a uniform powder blend of T3 by trituration with a placebo blend of microcrystalline cellulose, maize starch, talc and ethylcellulose, stearic acid and/or stearic acid salt (as appropriate). Good blend homogeneity of the compositions has been found to be facilitated by the optimisation of drug particle size, excipients and trituration.

The compositions of the invention are useful in the sustained release of drugs into systemic circulation.

The compositions of the invention may be used to treat/prevent diseases/conditions in mammalian patients depending upon the therapeutic agent(s) which is/are employed. These include those against which the therapeutic agent(s) in question are known to be effective, and include those diseases/conditions specifically listed for the drugs in question in Martindale, *The Complete Drug Reference*, 34$^{th}$ Edition, Pharmaceutical Press (2005). When the composition of the invention comprises a thyroid hormone, such T3, the present invention provides a method of treatment of hypothyroidism, or congestive heart failure, in a warm-blooded animal suffering from or susceptible to such a condition.

The term "treatment" includes the therapeutic and/or prophylactic treatment of a condition.

The compositions of the invention have the advantage that they exhibit acceptable and reproducible homogeneity, a consistent release performance and a commercially-acceptable shelf-life. These advantages are particularly significant in the development of compositions comprising low solubility drug substances, which may also possess a very high potency (and therefore require a low dose) and/or inherently poor physical/chemical stability, such as T3.

The compositions of the invention may also have the advantage that they can be prepared using established pharmaceutical processing methods and employ materials that are approved for use in foods or pharmaceuticals or of like regulatory status.

Compositions of the invention may also have the advantage that they may be more efficacious than, be less toxic than, be longer acting than, produce fewer side effects than, and/or have a better pharmacokinetic profile than, and/or have other useful pharmacological, physical, or chemical properties over, pharmaceutical compositions known in the prior art, whether for use in the treatment of hypothyroidism, or congestive heart failure, or otherwise.

BRIEF DESCRIPTION OF THE SEVERAL VIEWS OF THE DRAWINGS

The foregoing summary, as well as the following detailed description of the invention, will be better understood when read in conjunction with the appended drawings. For the purpose of illustrating the invention, there are shown in the drawings embodiments which are presently preferred. It should be understood, however, that the invention is not limited to the precise arrangements and instrumentalities shown. In the drawings.

DETAILED DESCRIPTION OF THE INVENTION

Example 1

Figure 1:
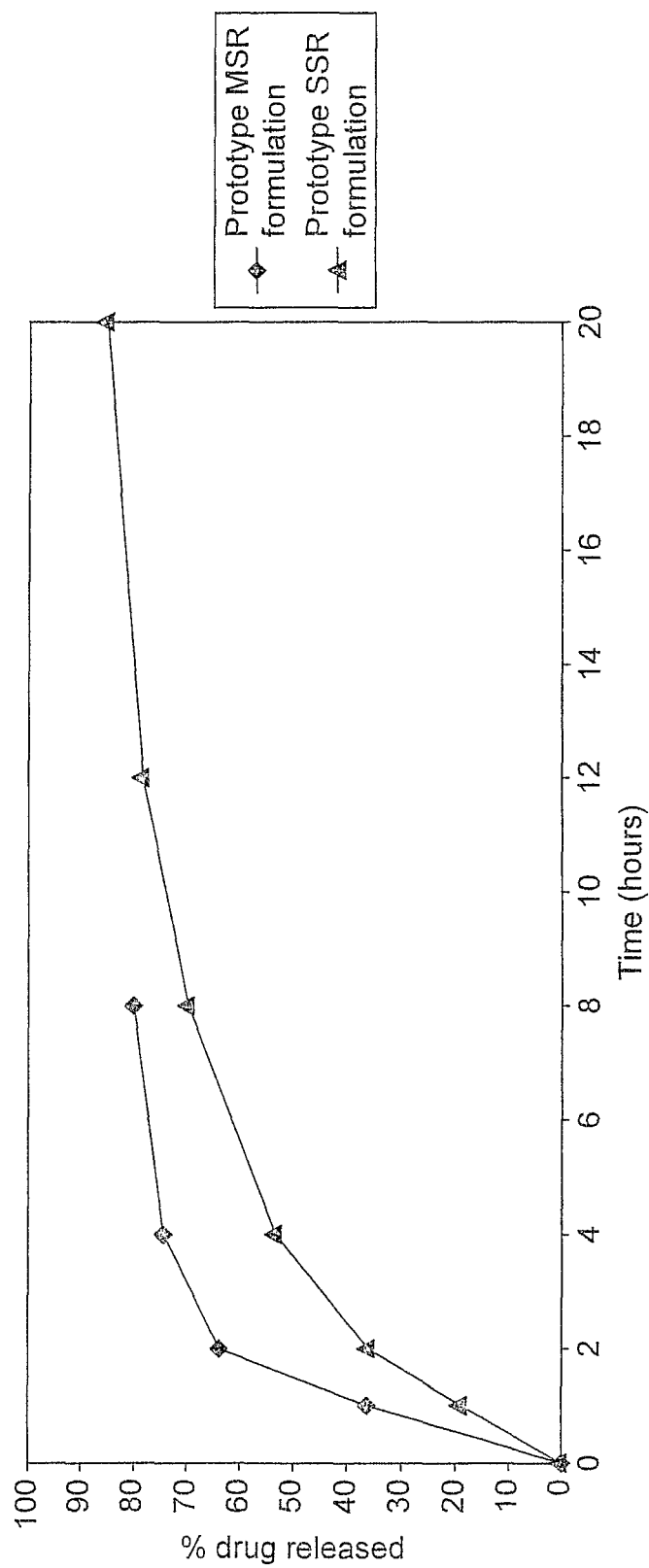
FIG. 1 is a graph showing in vitro drug release of T3 from MSR and SSR compositions, obtained by way of Examples 1 and 2 below, in pH 7.4 phosphate buffer USP.

Preparation and Dissolution Testing of a MSR T3 Formulation

Preparation of Placebo Blend

The manufacturing process involved initially preparing a placebo powder blend by sieving (using a 0.59 mm stainless steel sieve) and blending together 330 grams of microcrystalline cellulose USP/NF, PhEur (Avicel PH101, FMC Biopolymer, Ireland), 165 grams of extra white maize starch PhEur, USP/NF (Roquette, Italy) and 55 grams of talc PhEur, USP (Luzenac, UK). The powder blend was mixed using a Turbula T2 mixer (Glen Creston Ltd, UK) on speed setting 2 for 10 minutes.

Preparation of Blend Concentrate Containing 0.02% w/w Liothyronine

A uniform powder blend concentrate composition containing 0.02% w/w liothyronine (Liothyronine Sodium Oral, Biochemie, Austria) was then prepared by means of a comprehensive multi-stage trituration and using drug substance of a particle size less than 25 microns. One hundred milligrams of liothyronine sodium and 4.9 grams of placebo blend were dispensed into separate weighing boats. A small quantity of the 4.9 grams of placebo blend was transferred to a glass mortar and the 100 milligrams of drug substance passed through a 0.59 mm stainless steel sieve onto the placebo blend. A further small quantity of the 4.9 grams of placebo blend was transferred to the weighing boat previously containing the drug and the weighing boat was rinsed to incorporate any remaining liothyronine. The powder was transferred to the mortar through the sieve. The process was repeated using further quantities of the 4.9 grams of placebo blend, triturating and sieving each aliquot, until all the dispensed blend had been transferred to the mortar. The powders were gently mixed for 10 minutes using the pestle and mortar and then transferred to a 120 ml amber glass jar and blended using a Turbula T2 mixer for 10 minutes on speed setting 2.

A further 5 grams of placebo blend was dispensed into a small weighing boat and transferred to the glass mortar. The fresh placebo blend was mixed around the mortar to incorporate any remaining liothyronine. The contents of the amber glass jar and the mortar were then passed through a 0.59 mm stainless steel sieve onto a large sheet of paper, gently mixed using a palette knife and transferred to the 120 ml amber glass jar. The contents of the jar were blended using a Turbula T2 mixer for 10 minutes on speed setting 2.

A further 10 grams of placebo blend was dispensed into a weighing boat and together with the contents of the glass jar, were passed through a 0.59 mm stainless steel sieve onto the paper, gently mixed using a palette knife and transferred to the 120 ml amber glass jar. The contents of the jar were blended using a Turbula T2 mixer for 10 minutes on speed setting 2.

A further 20 grams of placebo blend was dispensed into a weighing boat and together with the contents of the glass jar, were passed through a 0.59 mm stainless steel sieve onto the paper, gently mixed using a palette knife and transferred to a 2000 ml polypropylene jar. The contents of the jar were blended using a Turbula T2 mixer for 10 minutes on speed setting 2.

The dilution process was repeated by triturating further quantities of 40 grams, 80 grams, 160 grams and 180 grams of placebo blend with the liothyronine blend until a blend concentration of 0.02% w/w liothyronine sodium and a final blend quantity of 500 grams was obtained.

Preparation and Processing of Final Blend 100 grams of maize starch, 50 grams of talc and 100 g of ethylcellulose (Aqualon® EC T10 Pharm NF/EP) were dispensed and passed though a 0.59 mm stainless steel sieve onto paper and gently mixed using a palette knife. These excipients were then transferred into a 2000 ml polypropylene jar and blended using a Turbula T2 mixer for 10 minutes on speed setting 2. The ethylcellulose blend, together with 250 grams of liothyronine sodium concentrate blend 0.02% w/w, were then transferred into the bowl of a Kenwood KM400 processor and dry mixed for 2 minutes on low speed setting.

The resulting final blend (500 grams) containing 0.01% w/w liothyronine (equivalent to 10 micrograms of liothyronine sodium per 50 mg) was then wet granulated to an appropriate end point using ultrapure water (320 ml; Elga, UK) as the granulating fluid. An appropriate end point was achieved when a heavy free-flowing granule (wet mass) was obtained. The wet mass was passed through an Alexanderwerk GA65 Extruder (Remscheid, Germany) fitted with a 1 mm diameter perforated cylinder rotating at 100 rpm. The resulting extrudate was transferred to a Caleva Model 380 Spheroniser (Dorset, UK) fitted with a plate of cross hatch geometry. A spheronization rotation speed of 550 rpm and a residence time of 6 minutes were found to be optimum for sphere formation. Product was dried to a moisture content of typically less than 3% w/w using a Aeromatic Strea-1 fluidised bed drier (Bubendorf, Switzerland) and passed through a 1.4 mm mesh sieve and over a 0.59 mm mesh sieve to remove any oversize product and/or fines. The moisture content was determined on crushed pellets using a Mettler Toledo Halogen HG53 moisture balance (Greifensee, Switzerland).

Dissolution Testing

The in vitro drug release was evaluated using a Sotax AT7 automated dissolution system (Basel, Switzerland) in accordance with United States Pharmacopoeia method II (USP28/NF23, United States Pharmacopoeia Convention, Rockville, Md., USA, 2002). Testing was performed using pH 7.4 phosphate buffer USP (500 ml) at 37° C. and a paddle rotation speed of 100 rpm.

2 grams of product were placed into each vessel and 2 ml samples of dissolution media removed at the appropriate time intervals. Samples were analysed for liothyronine using an Agilent 1100 LCMS system (Wokingham, UK) with matrix matched calibration and quality control standards. The liquid chromatography involved the use of a mobile phase of methanol and 1% acetic acid (65:35) at a flow rate of 1 ml/min and a Genesis C18 4µ 150×4.6 mm separating column. A mass spectrometer monitored the T3 and T2 ions in positive mode (with an m/z of 651.9 and 525.9 respectively). (T2 is 3,5-diiodo-L-thyronine and was used as an internal standard during dissolution testing).

Table 1 shows the composition, and FIG. 1 shows the dissolution profile, of the MSR T3 formulation.

TABLE 1

| Composition | % w/w |
|---|---|
| T3 | 0.01 |
| Avicel PH101 | 30 |
| Maize starch | 35 |
| Talc | 15 |
| Ethylcellulose T10 Pharm | 20 |

Example 2

Preparation and Dissolution Testing of a SSR T3 Formulation

Preparation of Placebo Blend

A placebo blend was prepared by sieving (using a 0.59 mm stainless steel sieve) and blending together 330 grams of microcrystalline cellulose USP/NF, PhEur (Avicel PH101, FMC Biopolymer, Ireland), 55 grams of extra white maize starch PhEur, USP/NF (Roquette, Italy) and 165 grams of talc PhEur, USP (Luzenac, UK). The placebo powder blend was mixed using a Turbula T2 mixer (Glen Creston Ltd, UK) on speed setting 2 for 10 minutes.

Preparation of Blend Concentrate Containing 0.02% w/w Liothyronine

A uniform powder blend concentrate composition containing 0.02% w/w liothyronine sodium was prepared using the method described in Example 1.

Preparation and Processing of Final Blend 100 grams of maize starch, 100 grams of calcium stearate USP, PhEur (Oleotec, Cheshire, UK) and 50 g of stearic acid PhEur (Oleotec) were dispensed and passed though a 0.59 mm stainless steel sieve onto paper and gently mixed using a palette knife. These excipients were then transferred into a 2000 ml polypropylene jar and blended using a Turbula T2 mixer for 10 minutes on speed setting 2. The stearate blend, together with 250 grams of liothyronine sodium blend 0.02% w/w, were then transferred into the bowl of a Kenwood KM400 processor and dry mixed for 2 minutes on low speed setting.

The resulting final blend (500 grams) containing 0.01% w/w liothyronine (equivalent to 10 micrograms of liothyronine sodium per 50 mg), 20% w/w calcium stearate and 10% w/w stearic acid was then wet granulated and processed as described in Example 1.

Dissolution Testing

The in vitro drug release profile of the SSR T3 formulation was evaluated as described in Example 1.

Table 2 shows the composition, and FIG. 1 shows the dissolution profile, of the SSR T3 formulation.

TABLE 2

| Composition | % w/w |
|---|---|
| T3 | 0.01 |
| Avicel PH101 | 30 |
| Maize starch | 25 |
| Talc | 15 |
| Calcium stearate | 20 |
| Stearic acid | 10 |

Example 3

Preparation and Dissolution Testing of a Sustained Release T3 Composition Containing 25% w/w Calcium Stearate and 10% w/w Stearic Acid Preparation of Placebo Blend A placebo blend containing microcrystalline cellulose, starch and talc was prepared using the quantities and method described in Example 2.

Preparation of Blend Concentrate Containing 0.02% w/w Liothyronine

A uniform powder blend concentrate composition containing 0.02% w/w liothyronine sodium was prepared using the method described in Example 1.

Preparation and Processing of Final Blend 75 grams of maize starch, 125 grams of calcium stearate and 50 g of stearic acid were dispensed, sieved and processed together with 250 grams of liothyronine blend concentrate using the procedure described in Example 2.

The resulting final blend (500 grams) containing 0.01% w/w liothyronine (equivalent to 10 micrograms of liothyronine sodium per 50 mg), 25% w/w calcium stearate and 10% w/w stearic acid was then wet granulated and processed as described in Example 1.

The composition of Example 3 is shown in Table 3.

Dissolution Testing

The in vitro drug release profile was evaluated as described in Example 1.

Figure 2:
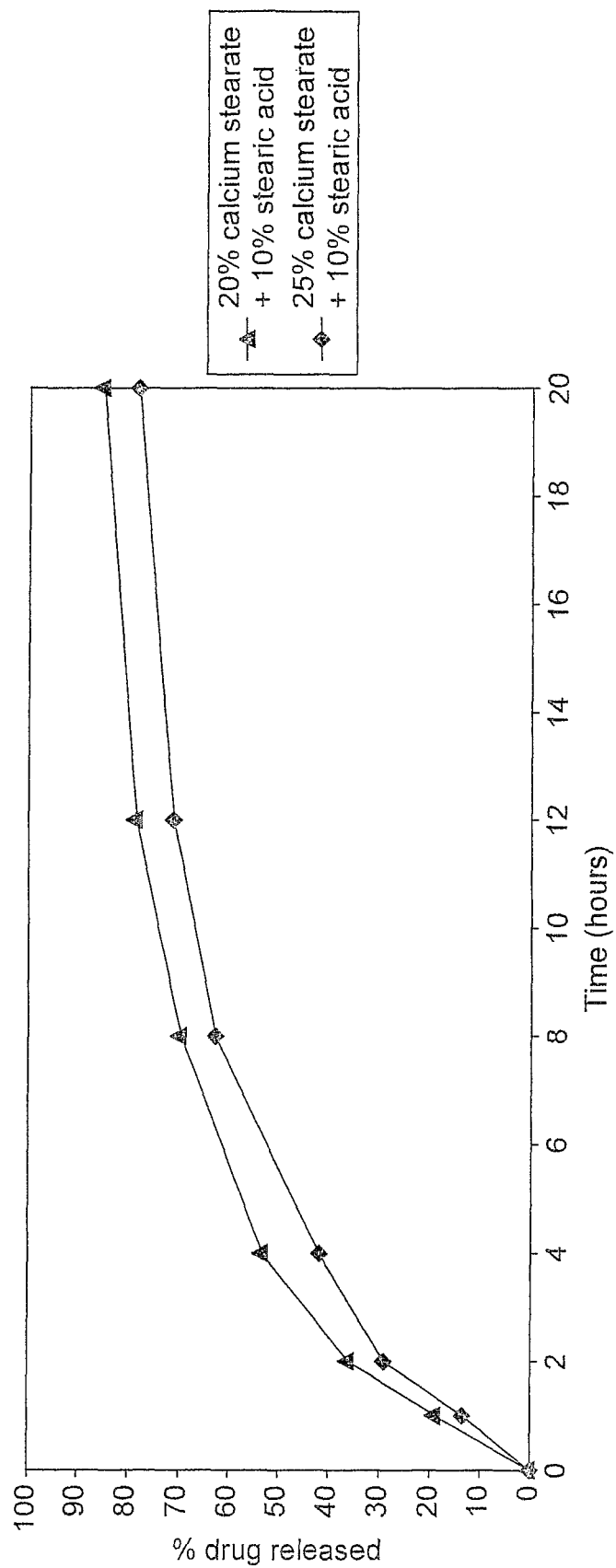
FIG. 2 is a graph showing in vitro drug release of T3 from sustained release compositions containing calcium stearate and stearic acid, obtained by way of Examples 2 and 3 below, in pH 7.4 phosphate buffer USP.

FIG. 2 shows the slowing effect of increasing the concentration of calcium stearate to 25% w/w on the in vitro dissolution profile, compared with the SSR formulation described in Example 2, which contains 20% w/w calcium stearate.

TABLE 3

| Composition | % w/w |
|---|---|
| T3 | 0.01 |
| Avicel PH101 | 30 |
| Maize starch | 20 |
| Talc | 15 |
| Calcium stearate | 25 |
| Stearic acid | 10 |
| Granulating water | 320 ml |

Example 4

Preparation and Dissolution Testing of a Sustained Release T3 Composition Containing 20% w/w Calcium Stearate in the Absence of Stearic Acid Preparation of Placebo Blend A placebo blend containing microcrystalline cellulose, starch and talc was prepared using the quantities and method described in Example 1.

Preparation of Blend Concentrate Containing 0.02% w/w Liothyronine

A uniform powder blend concentrate composition containing 0.02% w/w liothyronine sodium was prepared using the method described in Example 1.

Preparation and Processing of Final Blend 100 grams of maize starch, 50 g of talc and 100 grams of calcium stearate were dispensed, sieved and processed together with 250 grams of liothyronine blend concentrate using the procedure described in Example 2.

The resulting final blend (500 grams) containing 0.01% w/w liothyronine (equivalent to 10 micrograms of liothyronine sodium per 50 mg) and 20% w/w calcium stearate was then wet granulated and processed as described in Example 1.

The composition of Example 4 is shown in Table 4.

Dissolution Testing

The in vitro drug release profile was evaluated as described in Example 1.

Figure 3:
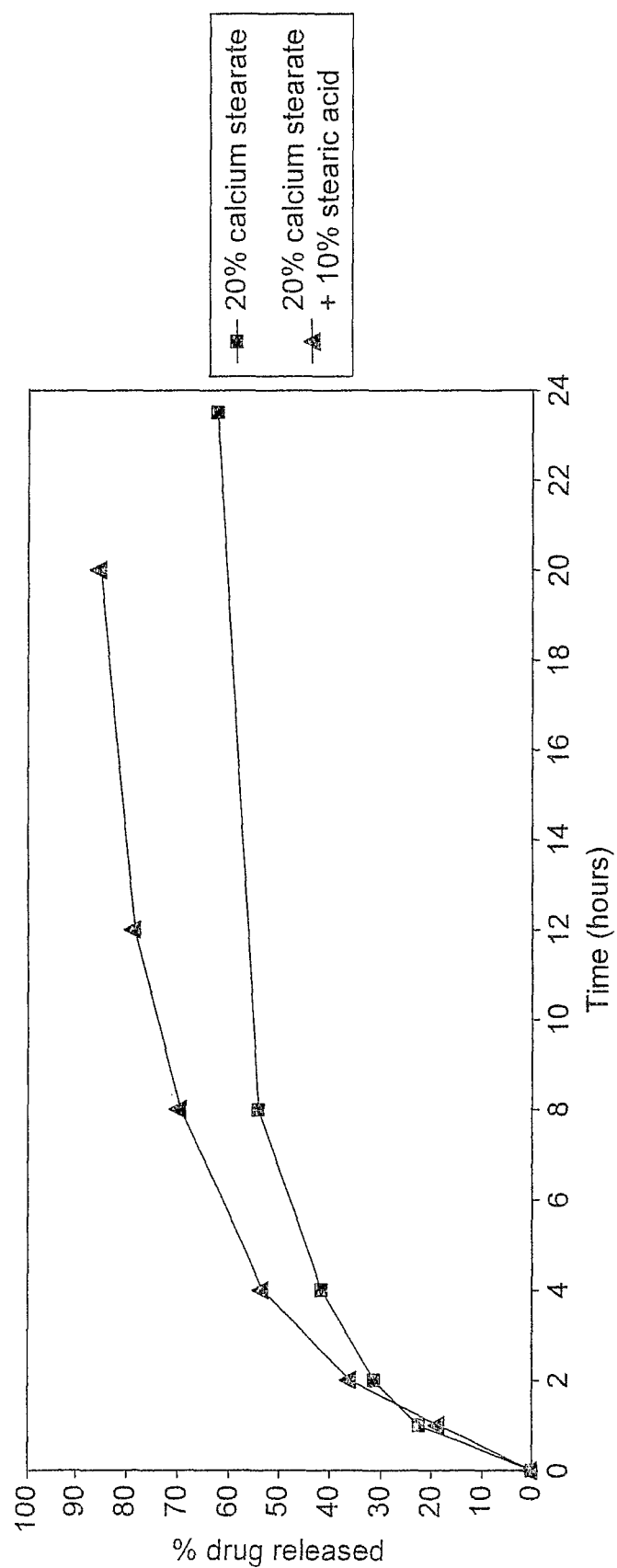
FIG. 3 is a graph showing in vitro drug release of T3 from sustained release compositions containing calcium stearate, obtained by way of Examples 2 and 4 below, in pH 7.4 phosphate buffer USP.

FIG. 3 shows the effect of the absence of stearic acid on the in vitro release of T3 from SSR compositions containing 20% w/w calcium stearate in the presence and absence of stearic acid (compositions prepared according to Examples 2 and 3, respectively). These data support the observation that compositions containing stearic acid surprisingly have a tendency to partially disintegrate during in vitro dissolution testing and thus advantageously facilitate more complete release of drug.

TABLE 4

| Composition | % w/w |
|---|---|
| T3 | 0.01 |
| Avicel PH101 | 30 |
| Maize starch | 35 |
| Talc | 15 |
| Calcium stearate | 20 |
| Granulating water | 330 ml |

Example 5

Preparation and Dissolution Testing of Sustained Release T3 Compositions Containing Stearic Acid

Examples 5.1 and 5.2

Preparation of Placebo Blend 550 grams of placebo blend was prepared containing 183.15 grams of microcrystalline cellulose, 275 grams of extra white maize starch and 91.85 grams of talc using the method described in Example 1.

Preparation of Blend Concentrate Containing 0.02% w/w Liothyronine

A uniform powder blend concentrate composition containing 0.02% w/w liothyronine sodium was prepared using the method described in Example 1.

Preparation and Processing of Final Blend [Quantities Used in Example 5.2]

66.6 [66.4] grams of microcrystalline cellulose, 100 [49.9] grams of maize starch, 33.4 [33.5] grams of talc and 50 [99.9] grams of stearic acid powder were dispensed, sieved and processed together with 250 [249.7] grams of liothyronine blend concentrate using the procedure described in Example 2.

The resulting final blend (500 [499.4] grams) containing 0.01% w/w liothyronine (equivalent to 10 micrograms of liothyronine sodium per 50 mg) and 10% [20%] w/w stearic acid was then wet granulated and processed as described in Example 1. The volume of granulating water used during processing is shown in Table 5.

Example 5.3

Preparation of Placebo Blend

Placebo blend containing microcrystalline cellulose, starch and talc was prepared as described in Example 1.

Preparation of Blend Concentrate Containing 0.02% w/w Liothyronine

A uniform powder blend concentrate composition containing 0.02% w/w liothyronine sodium was prepared using the method described in Example 1.

Preparation and processing of Final Blend 50 grams of microcrystalline cellulose, 50 grams of talc and 150 grams of stearic acid powder were dispensed, sieved and processed together with 250 grams of liothyronine blend concentrate using the procedure described in Example 2.

The resulting final blend (500 grams) containing 0.01% w/w liothyronine (equivalent to 10 micrograms of liothyronine sodium per 50 mg) and 30% w/w stearic acid was then wet granulated and processed as described in Example 1. The volume of granulating water used during processing is shown in Table 5.

Examples 5.4 and 5.5

Preparation of Placebo Blend 550 grams of placebo blend was prepared containing 330 grams of microcrystalline cellulose, 55 grams of extra white maize starch, 55 grams of talc and 110 grams of stearic acid powder using the method described in Example 1.

Preparation of Blend Concentrate Containing 0.02% w/w Liothyronine

A uniform powder blend concentrate composition containing 0.02% w/w liothyronine sodium was prepared using the method described in Example 1.

Preparation and Processing of Final Blend [Quantities Used in Example 5.5]

50 [0] grams of microcrystalline cellulose, 50 [50] grams of talc and 150 [200] grams of stearic acid powder were dispensed, sieved and processed together with 250 [250] grams of liothyronine blend concentrate using the procedure described in Example 2.

The resulting final blend (500 grams) containing 0.01% w/w liothyronine (equivalent to 10 micrograms of liothyronine sodium per 50 mg) and 40% [50%] w/w stearic acid was then wet granulated and processed as described in Example 1. The volume of granulating water used during processing is shown in Table 5.

Dissolution Testing

The in vitro drug release profile was evaluated for Examples 5.1 to 5.5 as described in Example 1.

Figure 4:
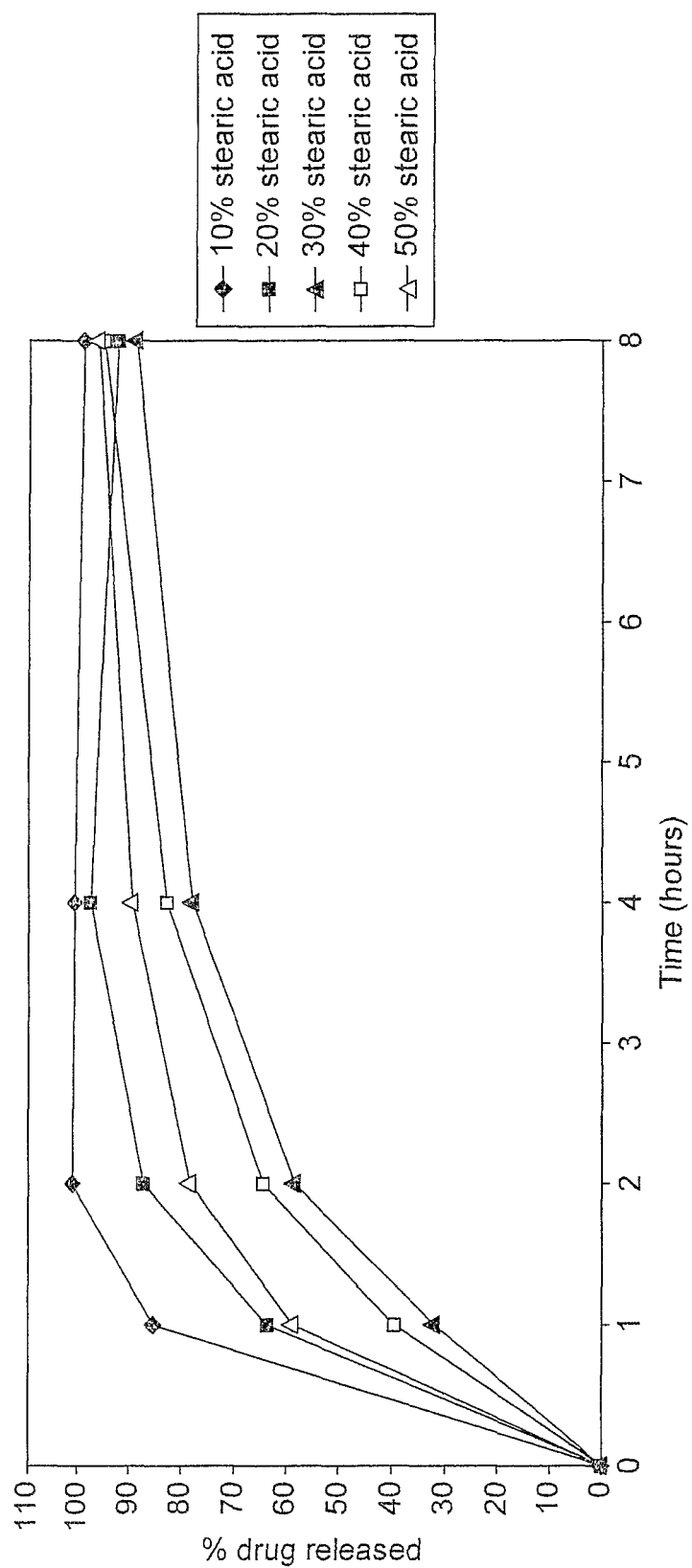
FIG. 4 is a graph showing in vitro drug release of T3 from sustained release compositions containing stearic acid, obtained by way of Example 5 below, in pH 7.4 phosphate buffer USP.

FIG. 4 shows the effect increasing concentrations of stearic acid in sustained release liothyronine bead formulations. Progressive slowing of drug release is observed from compositions with increasing levels of stearic acid up to 30% w/w. Surprisingly, concentrations of stearic acid in excess of 30% w/w result in a progressive increase in the rate of drug release, which is attributed to a tendency for the dosage form to partially disintegrate during testing.

The composition of sustained release formulations containing stearic acid is shown in Table 5.

TABLE 5

| Composition | Example number | | | | |
|---|---|---|---|---|---|
| | 5.1 | 5.2 | 5.3 | 5.4 | 5.5 |
| | % w/w | | | | |
| T3 | 0.01 | 0.01 | 0.01 | 0.01 | 0.01 |
| Avicel PH101 | 30 | 30 | 40 | 40 | 30 |
| Maize starch | 45 | 35 | 15 | 5 | 5 |
| Talc | 15 | 15 | 15 | 15 | 15 |
| Stearic acid | 10 | 20 | 30 | 40 | 50 |
| Granulating water | 335 ml | 320 ml | 310 ml | 290 ml | 260 ml |

Example 6

Preparation and Dissolution Testing of Sustained Release T3 Compositions Containing Ethylcellulose (Aqualon® EC T10 Pharm)

Examples 6.1 and 6.2

Preparation of Placebo Blend

A placebo blend containing microcrystalline cellulose, maize starch and talc was prepared using the quantities and method described in Example 2.

Preparation of Blend Concentrate Containing 0.02% w/w Liothyronine

A uniform powder blend concentrate composition containing 0.02% w/w liothyronine sodium was prepared using the method described in Example 1.

Preparation and Processing of Final Blend [Quantities Used in Example 6.2]

100 [50] grams of maize starch and 150 [200] grams of ethylcellulose T10 Pharm were dispensed, sieved and processed together with 250 [250] grams of liothyronine blend concentrate using the procedure described in Example 1.

The resulting final blend (500 grams) containing 0.01% w/w liothyronine (equivalent to 10 micrograms of liothyronine sodium per 50 mg) and 30% [40%] w/w ethylcellulose T10 Pharm was then wet granulated and processed as described in Example 1. The volume of granulating water used during processing is shown in Table 6.

Dissolution Testing

The in vitro drug release profiles for Examples 6.1 and 6.2 were evaluated as described in Example 1.

Figure 5:
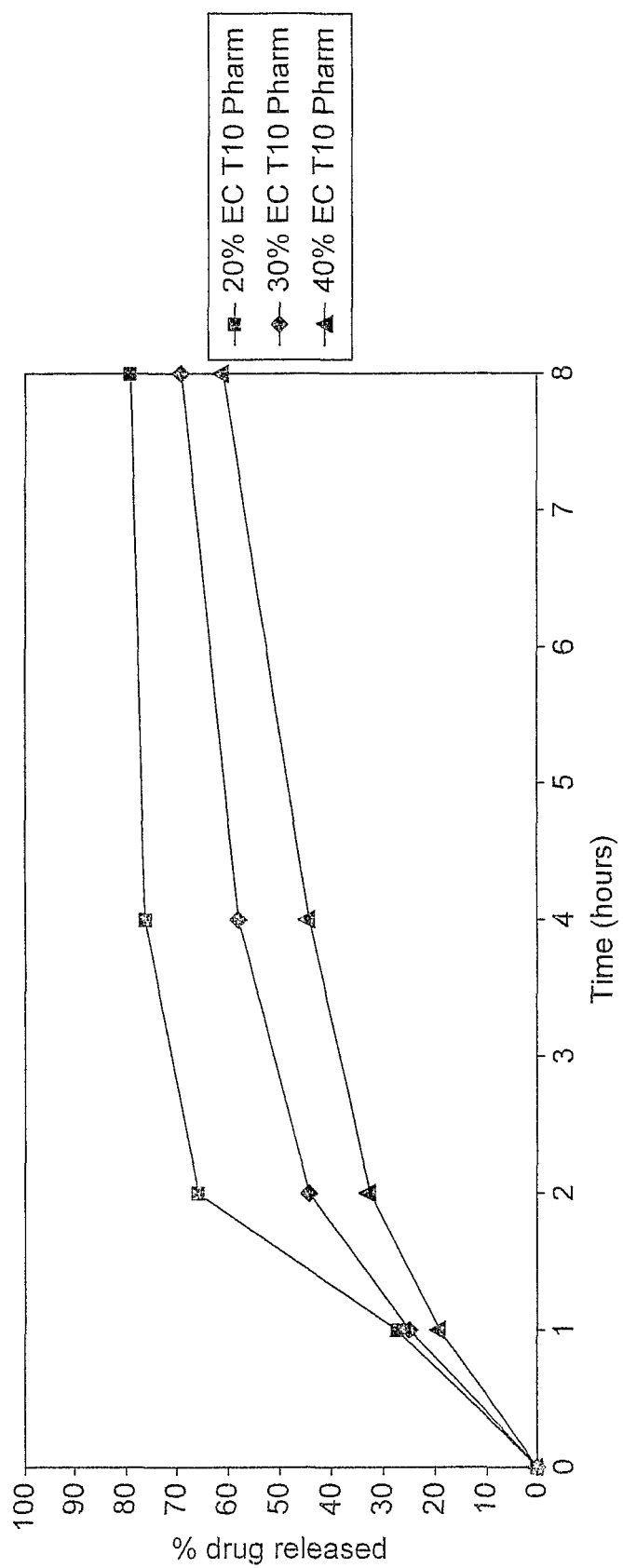
FIG. 5 is a graph showing in vitro drug release of T3 from sustained release compositions containing ethylcellulose, obtained by way of Examples 1 and 6 below, in pH 7.4 phosphate buffer USP.

FIG. 5 shows the effect of increasing concentrations of ethylcellulose T10 Pharm in sustained release T3 compositions (prepared as described in Examples 1, 6.1 and 6.2, respectively). A progressive slowing of in vitro drug release is noted for sustained release liothyronine sodium formulations with increasing ethylcellulose concentration.

The composition of sustained release formulations containing ethylcellulose T10 Pharm is shown in Table 6.

TABLE 6

| Material | Example number | |
|---|---|---|
| | 6.1 | 6.2 |
| | % w/w | |
| T3 | 0.01 | 0.01 |
| Avicel PH101 | 30 | 30 |

TABLE 6-continued

| | Example number | |
|---|---|---|
| | 6.1 | 6.2 |
| Material | % w/w | |
| Maize starch | 25 | 15 |
| Talc | 15 | 15 |
| Ethylcellulose | 30 | 40 |
| Granulating water | 330 ml | 340 ml |

Example 7

Preparation and Dissolution Testing of Sustained Release T3 Compositions Containing Calcium Stearate and Stearic Acid and the Effect of Applying a Gastroresistant Coating Examples 7.1, 7.2 and 7.3

Preparation of Placebo Blend

A placebo blend containing microcrystalline cellulose, starch and talc was prepared using the quantities and method described in Example 1.

Preparation of Blend Concentrate Containing 0.04% w/w Liothyronine

A uniform powder blend concentrate composition containing 0.04% w/w liothyronine sodium was prepared using the method described in Example 1, except that 220 mg of liothyronine sodium was used in place of 100 mg.

Preparation and Processing of Final Blend 50 grams of maize starch, 100 grams of calcium stearate, 50 g of stearic acid and 50 g of talc were dispensed, sieved and processed together with 250 grams of liothyronine blend concentrate using the procedure described in Example 2.

The resulting final blend (500 grams) containing 0.02% w/w liothyronine (equivalent to 10 micrograms of liothyronine sodium per 50 mg) was then wet granulated and processed as described in Example 1.

The composition formed by the method described above is provided in Table 7 (Example 7.1).

Application of Gastroresistant Coating

Into a container was dispensed 878 grams of absolute ethanol. Into a glass beaker was weighed 70 grams of HPMCP-50 (ShinEtsu, Japan) which was dissolved by adding approximately 700 ml of the ethanol Ph Eur, USP (Fisher, UK) followed by stirring. Into the HPMCP solution was stirred 375 grams of water and then 7 grams of triethyl citrate NF (Morflex Inc., USA). In a separate small beaker 70 grams of talc Ph Eur, USP (Luzenac, UK) was mixed into a paste using some of the remaining ethanol and the paste was added to the HPMCP solution. The remaining ethanol was used to rinse any residual talc paste into the HPMCP solution.

200 grams of LT3 beads (Example 7.1) were coated using an Aeromatic Strea-1 fluidised bed coater fitted with a spray gun. The beads were transferred to the coater chamber and pre-warmed to a temperature of 50° C. The coating dispersion was sprayed onto the beads at a rate of approximately 4 grams/minute. To produce beads with a theoretical 3% w/w content of HPMCP-50 (Example 7.2), 120 g of coating dispersion was applied. A 30 gram sample of beads was removed for drug assay and dissolution purposes. To the remaining 170 grams of beads, an additional 68 g of coating solution was applied. These beads (Example 7.3) had a theoretical HPMCP content of 5% w/w. The final gastroresistant coating in Examples 7.2 and 7.3 comprised 47.6% w/w HPMCP HP-50, 4.8% w/w triethyl citrate and 47.6% w/w talc.

Dissolution Testing

The in vitro drug release profiles of the uncoated and HPMCP-coated beads was evaluated as described in Example 1 but using as the test media 0.1M hydrochloric acid, pH 7.4 phosphate buffer or a pH-change method (1 h in 0.1M HCl, followed by pH 7.4 buffer).

Figure 6:
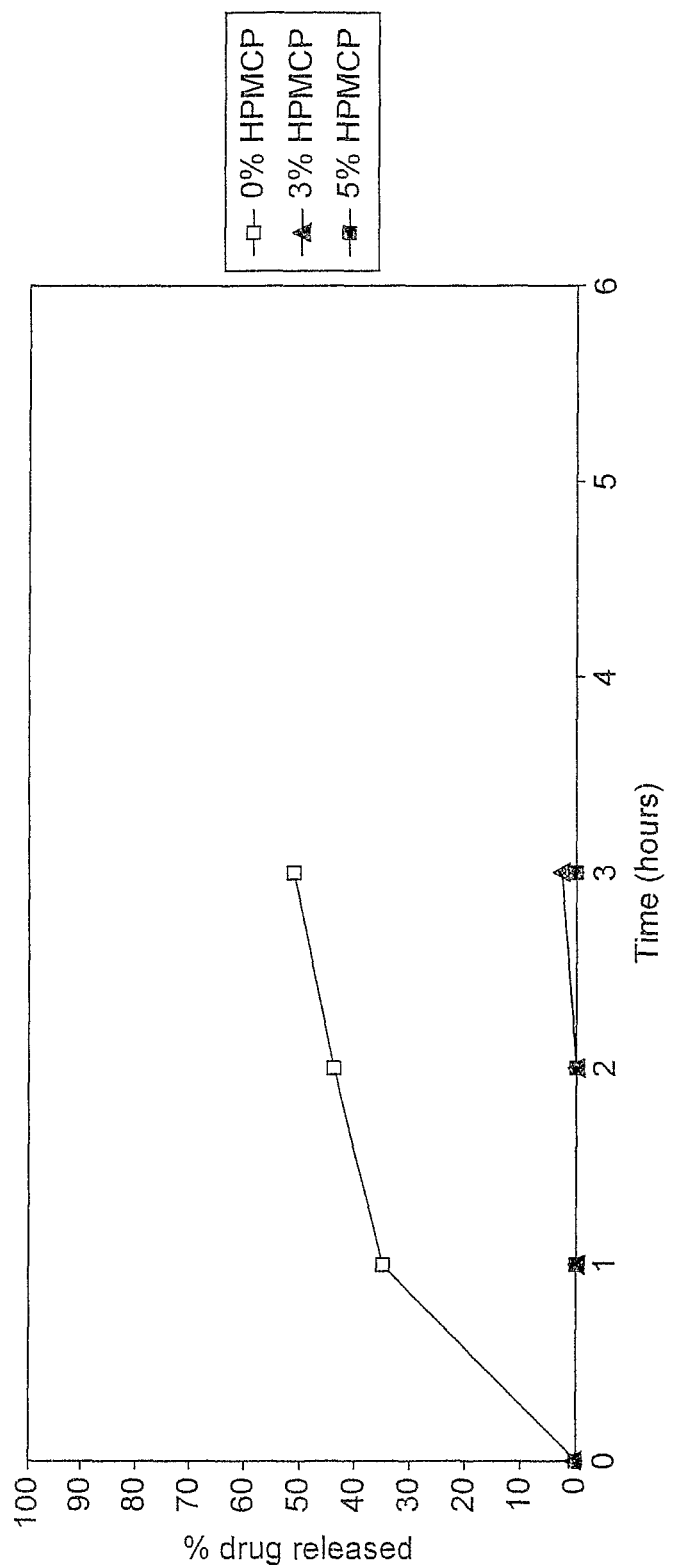
FIG. 6 is a graph showing in vitro drug release of T3 from sustained release compositions containing calcium stearate and stearic acid, obtained by way of Example 7 below, in 0.1M hydrochloric acid.

FIG. 6 shows the dissolution of beads with 0, 3 and 5% HPMCP coating in 0.1M HCl. The 3% w/w and 5% w/w HPMCP coats both provided excellent resistance to T3 release in acid.

Figure 7:
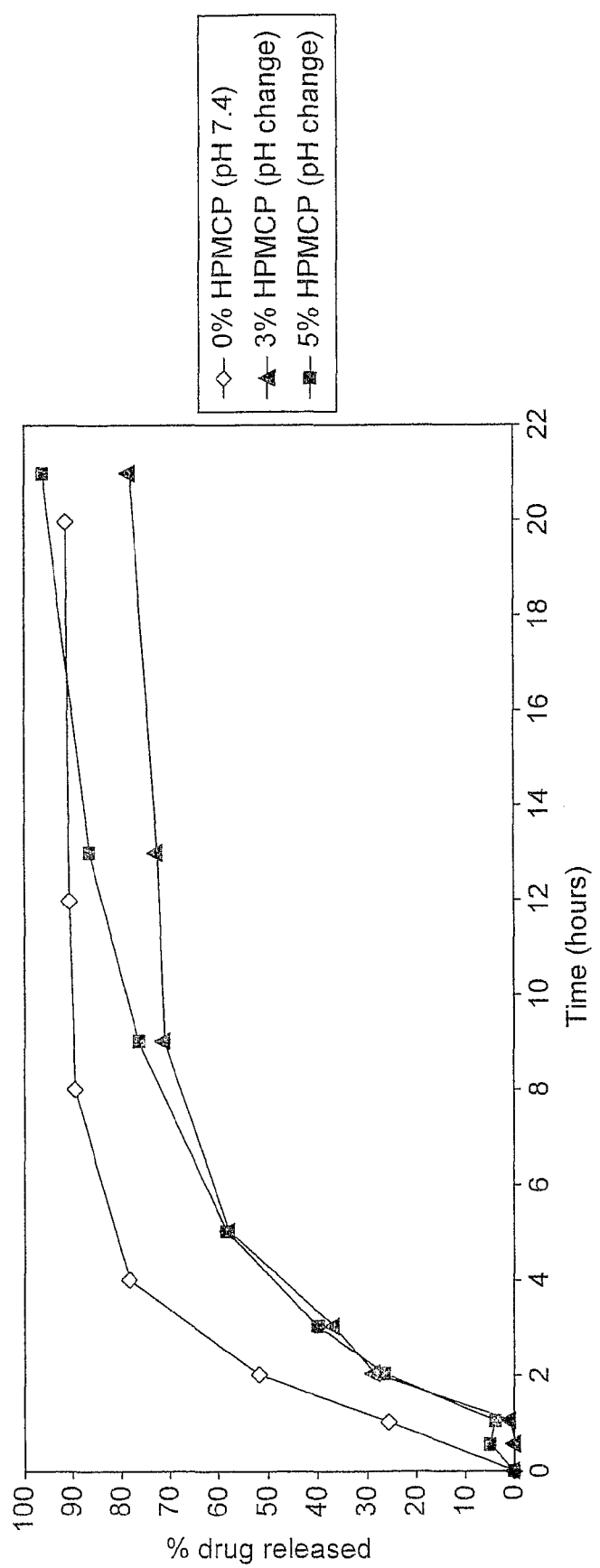
FIG. 7 is a graph showing in vitro drug release of T3 from sustained release compositions containing calcium stearate and stearic acid, obtained by way of Example 7 below, in pH 7.4 phosphate buffer and using a pH change method (1 h in 0.1M hydrochloric acid followed by pH 7.4 phosphate buffer USP)

FIG. 7 shows a slower release of T3 from the bead formulation at pH 7.4 compared to 0.1M HCl. For the HPMCP-coated beads tested using a pH-change process, there was a small delay in drug release at pH 7.4 but, in addition, the subsequent rate of drug release appeared to be slower compared to the beads with no HPMCP coating.

TABLE 7

| Composition | % w/w |
|---|---|
| T3 | 0.02 |
| Avicel PH101 | 30 |
| Maize starch | 25 |
| Talc | 15 |
| Calcium stearate | 20 |
| Stearic acid | 10 |
| Granulating water | 300 ml |

Example 8

Preparation and Dissolution Testing of Sustained Release T3 Compositions Containing Ethylcellulose and the Effect of Applying a Gastroresistant Coating Examples 8.1, 8.2 and 8.3

Preparation of Placebo Blend

A placebo blend containing microcrystalline cellulose, starch and talc was prepared using the quantities and method described in Example 1.

Preparation and Processing of Final Blend 100 grams of maize starch, 50 grams of talc and 100 g of ethylcellulose were dispensed, sieved and processed together with 250 grams of liothyronine blend concentrate (Example 7) using the procedure described in Example 1.

The resulting final blend (500 grams) containing 0.02% w/w liothyronine (equivalent to 10 micrograms of liothyronine sodium per 50 mg) was then wet granulated and processed as described in Example 1. The volume of granulating water used during processing is shown in Table 8.

The composition formed by the method described above is provided in Table 8 (Example 8.1).

Application of Gastro-Resistant Coating

The composition described above (Example 8.1) was coated as described for Example 7 to produce T3 beads with a theoretical HPMCP content of 3% w/w (Example 8.2) and 5% w/w (Example 8.3).

Dissolution Testing

In vitro dissolution tests were performed as described for Example 7.

Figure 8:
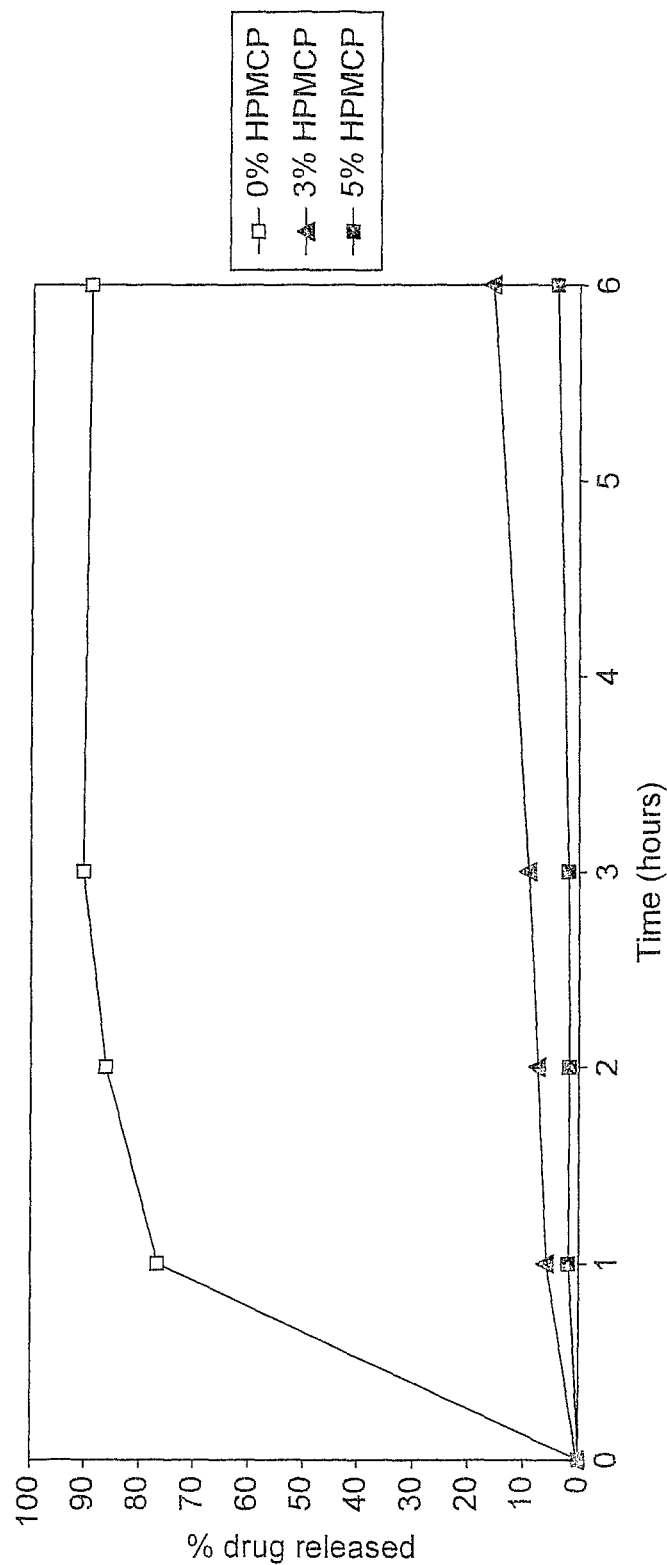
FIG. 8 is a graph showing in vitro drug release of T3 from sustained release compositions containing ethylcellulose, obtained by way of Example 8 below, in 0.1M hydrochloric acid.

FIG. 8 shows the dissolution of beads with 0, 3 and 5% HPMCP coating in 0.1M HCl. Both levels of HPMCP were effective in reducing the release of T3 in acid media, although 5% provided greater resistance to release. It should be noted that approximately 80% of T3 had been released after 1 hour from beads with no HPMCP coating.

Figure 9:
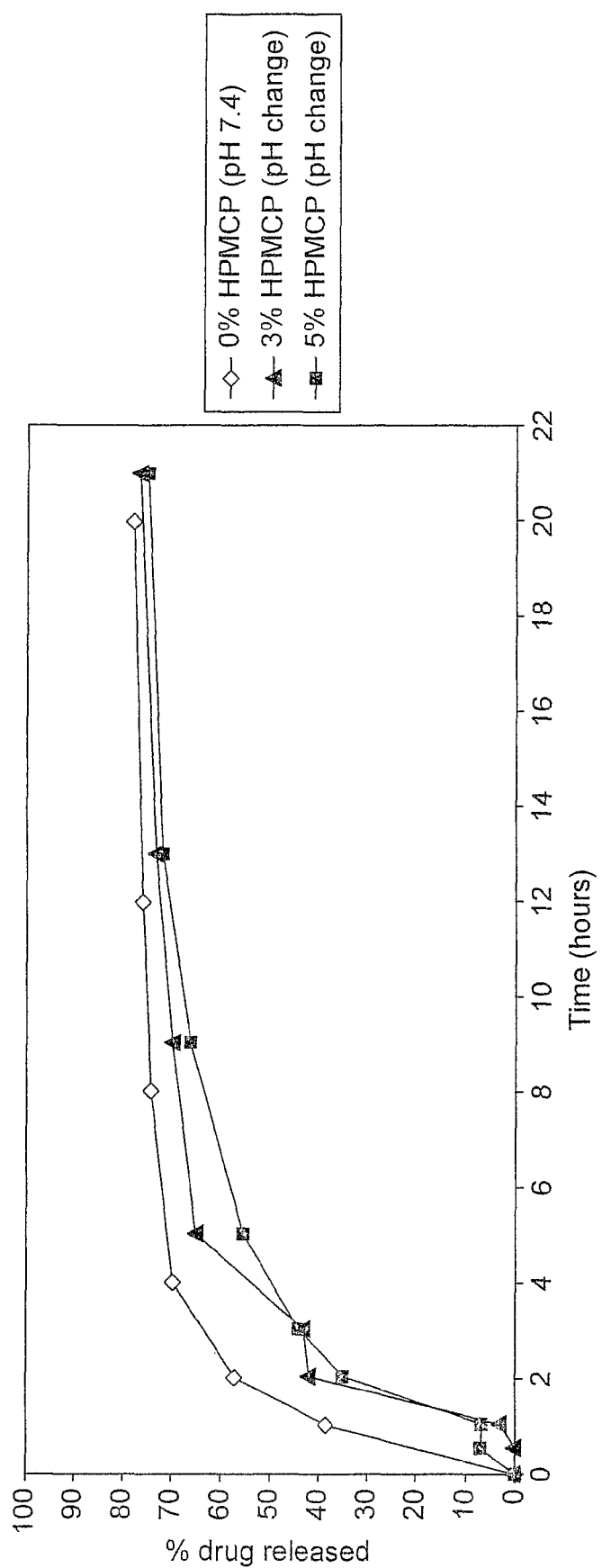
FIG. 9 is a graph showing in vitro drug release of T3 from sustained release compositions containing ethylcellulose, obtained by way of Example 8 below, in pH 7.4 phosphate buffer and using a pH change method (1 h in 0.1M hydrochloric acid followed by pH 7.4 phosphate buffer USP).

In FIG. 9 the dissolution of T3 beads with no HPMCP coating at pH 7.4 is compared to beads with 3% and 5% coating using a pH change method. For the beads with no HPMCP coating, less than 40% of T3 was released after 1 hour, which illustrates the sensitivity of this formulation to pH i.e. 80% released after 1 hour in acid (FIG. 8). Using the pH change method, there was slight delay in drug release at pH 7.4 in the HPMCP-coated samples.

TABLE 8

| Composition | % w/w |
|---|---|
| T3 | 0.02 |
| Avicel PH101 | 30 |
| Maize starch | 35 |
| Talc | 15 |
| Ethylcellulose T10 Pharm | 20 |
| Granulating water | 320 ml |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A sustained release pharmaceutical composition consisting of (I) a matrix form comprising:
   (a) 0.001-60% w/w of liothyronine or the sodium salt of liothyronine;
   (b) 10-60% w/w of microcrystalline cellulose;
   (c) 10-60% w/w of a diluent;
   (d) 5-25% w/w of a glidant; and
   (e) one or more of ethylcellulose having an ethoxyl substitution of from 47 to 51% and a viscosity (5% solution in 80/20 toluene/ethanol) of from 5 to 40 cps, stearic acid and a salt of stearic acid, in an amount such that the total weight of component (e) is from 10 to 60% w/w; and (II) an optional enteric coating, coating the matrix.

2. A composition as claimed in claim 1 obtained by a process comprising extrusion-spheronisation.

3. A composition as claimed in claim 1 in which component (e) of the matrix comprises from 20 to about 50% w/w of ethylcellulose, stearic acid or a salt of stearic acid or a combination thereof.

4. A composition as claimed in claim 1, wherein component (e) is ethylcellulose only.

5. A composition as claimed in claim 1, wherein the ethylcellulose has an ethoxyl substitution in the range 49.6 to 51.0% and a viscosity (5% solution in 80/20 toluene/ethanol) of 8 to 11 cps.

6. A composition as claimed in claim 1, wherein the amount of stearic acid present in the matrix is 30% w/w or below.

7. A composition as claimed in claim 1, wherein the amount of stearic acid in the matrix is from 10 to 25% w/w.

8. A composition as claimed in claim 1, wherein the amount of stearic acid salts present in the matrix is 50% w/w or below.

9. A composition as claimed in claim 1, wherein the amount of microcrystalline cellulose in the matrix is from 20 to 50% w/w.

10. A composition as claimed in claim 1, wherein the glidant is talc.

11. A composition as claimed in claim 1, wherein the amount of glidant in the matrix is from 10 to 20% w/w.

12. A composition as claimed in claim 1, wherein the diluent is starch.

13. A composition as claimed in claim 1, wherein the amount of diluent in the matrix is from 15 to 35% w/w.

14. A composition as claimed in claim 1, wherein the amount of liothyronine or the sodium salt of liothyronine in the matrix is from 0.002 to 50% w/w.

15. A composition as claimed in claim 1, which exhibits a release in an in vitro dissolution test of at least 50% of drug within a period of around 4 hours, and at least 70% within a period of around 6 hours.

16. A composition as claimed in claim 1, which exhibits a release in an in vitro dissolution test of at least 50% of drug within a period of around 8 hours, and at least 70% within a period of around 12 hours.

17. A composition as claimed in claim 15, in which the matrix comprises ethylcellulose, starch (as the diluent) and talc (as the glidant).

18. A composition as claimed in claim 17, in which the matrix comprises 0.001 to 1% w/w of liothyronine or a salt thereof; 20 to 40% w/w of microcrystalline cellulose; 15 to 55% w/w of starch, 10 to 20% w/w of talc; and 15 to 25% w/w of ethylcellulose.

19. A composition as claimed in claim 16, in which the matrix comprises stearic acid and/or a salt thereof, starch (as the diluent) and talc (as the glidant).

20. A composition as claimed in claim 19, in which the matrix comprises 0.001 to 1% w/w of liothyronine or a salt thereof; 20 to 40% w/w of microcrystalline cellulose; 15 to 35% w/w of starch, 5 to 20% w/w of talc; 10 to 30% w/w of calcium stearate; and 5 to 15% w/w of stearic acid.

21. A composition as claimed in claim 1, which is in the form of pellets.

22. A composition as claimed in claim 21, wherein the pellet diameter is from 0.1 to 2 mm.

23. A composition as claimed in claim 21, wherein the pellets are contained within hard capsules made from gelatin, hydroxypropylmethylcellulose, pullulan or starch.

24. A composition as claimed in claim 21, wherein the pellets consist essentially of liothyronine or the sodium salt of liothyronine, microcrystalline cellulose, a diluent, a glidant and ethylcellulose.

25. A process for the preparation of a composition as defined in claim 1, which comprises preparing a heavy granule or wet mass by mixing the ingredients with sufficient water to form a paste, passing the paste through an extruder, transferring the extrudate to a spheronizer, and then drying the particles so formed.

26. A method of providing sustained release of a drug into systemic circulation, which comprises administration of a composition as defined in claim 1 to a patient in need of such sustained release.

27. A method of treatment of congestive heart failure which comprises administration of a composition as defined in claim 1 to a patient in need of such treatment.

* * * * *

UNITED STATES PATENT AND TRADEMARK OFFICE
CERTIFICATE OF CORRECTION

| | | |
|---|---|---|
| PATENT NO. | : 8,460,702 B2 | Page 1 of 1 |
| APPLICATION NO. | : 12/097163 | |
| DATED | : June 11, 2013 | |
| INVENTOR(S) | : Alan Smith et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 520 days.

Signed and Sealed this
Twenty-third Day of December, 2014

Michelle K. Lee
*Deputy Director of the United States Patent and Trademark Office*